United States Patent [19]  [11]  4,228,106
Martan  [45]  Oct. 14, 1980

[54] PROCESS FOR PRODUCING BETA-BROMOETHYL AROMATIC COMPOUNDS

[75] Inventor: Michael Martan, Rehovot, Israel

[73] Assignee: M.C.P. - Chemical Processes Ltd., Rehovot, Israel

[21] Appl. No.: 46,256

[22] Filed: Jun. 7, 1979

[30] Foreign Application Priority Data

Jul. 6, 1978 [IL] Israel .......................................... 55092

[51] Int. Cl.$^2$ ............................................. C07C 17/08
[52] U.S. Cl. ..................................................... 570/197
[58] Field of Search ...................................... 260/651 F

[56] References Cited

U.S. PATENT DOCUMENTS

| | | | |
|---|---|---|---|
| 3,321,536 | 5/1967 | Plesmid | 260/651 R |
| 3,998,895 | 12/1976 | Schmerling | 260/651 R |
| 4,036,896 | 7/1977 | Schmerling | 260/651 R |

Primary Examiner—C. Davis
Attorney, Agent, or Firm—Haseltine, Lake & Waters

[57] ABSTRACT

The invention provides a process for producing beta-bromoethyl aromatic compounds comprising reacting hydrogen bromide with a vinyl aromatic compound in the presence of an azo radical initiator to effect the antimarkovnikoff addition of HBr to the vinyl double bond.

9 Claims, No Drawings

PROCESS FOR PRODUCING BETA-BROMOETHYL AROMATIC COMPOUNDS

The present invention relates to a process for making beta-bromo ethyl aromatic compounds via the antimarkovnikoff addition of HBr to olefinic compounds.

More specifically it relates to an improved process for preparing beta-bromoethyl aromatic compounds using certain radical initiators.

In U.S. Pat. Nos. 2,082,946 and 2,935,535 the antimarkovnikoff addition of HBr to olefinic compounds is effected by using peroxides such as benzoyl peroxides in relatively large quantities in order to avoid the formation of the alpha brominated compounds.

As it is recommended in these patents, the amount of peroxides used is in the range of 0.2 to 2% on the total weight of the solution which is a weight percent of the olefin of about 1 to 10%. As it is described in examples of U.S. Pat. No. 2,935,535, and as has also been confirmed by separate experiments, in order to prevent the formation of α-bromo compounds one should use peroxides such as benzoyl peroxide in quantities of 8-10% by weight to the olefin. It is to be noted, however, that the use of such large quantities of peroxides makes the process dangerous as well as expensive because of the relative high price of these peroxides.

As it is known, beta bromoethyl aromatic compounds are important intermediates for the synthesis of halogenated aromatic ring vinyl compounds useful as monomers for the preparation of self-extinguishing plastic materials. These products are also important intermediates for the synthesis of β-phenethyl esters which are important for the synthesis of drug and aroma materials as discussed in Israel Specification No. 54 335.

It is, therefore, important to provide a safe and inexpensive procedure for the production of beta-bromoethyl aromatic compounds free from the α-bromo isomer especially since the formation of α-bromo isomers lowers the yield and makes it tedious to purify the final products from the α-substituted derivatives.

It has now been unexpectedly discovered that it is possible to obtain, in very high selectivity, the beta-bromo derivate during the addition of HBr to vinyl aromatic compounds when azo radical initiator compounds are used, instead of peroxides as described in the previous patents. By using azo radical initiators, it has also now been found feasible to lower the radical initiator quantities to a level lower than 1 W% based on the olefin used. This fact renders the novel process of the present invention both safer and more economical.

Thus, according to the present invention, there is now provided a process for producing beta-bromo ethyl aromatic compounds comprising reacting hydrogen bromide with a vinyl aromatic compound in the presence of an azo radical initiator to effect the anti-markovnikoff addition of HBr to the vinyl double bond.

Preferably according to the present invention beta-bromoethyl benzenes are readily obtained by reacting HBr with vinyl aromatic compounds in the presence of an azo radical initiator compound while having the reactants dispersed or dissolved in an organic solvent.

According to the previous literature, such as U.S. Pat. No. 2,935,535, the solvent plays a key role in effecting the yield of the anti-markovnikoff product. It was claimed in this patent that this reaction should be carried out only in carbon tetrachloride or perchlorethylene. It has now been further surprisingly and unexpectedly found that the anti-markovnikoff addition of HBr to styrene could be carried in a large number of nonpolar solvents and is not restricted to CCl$_4$ which is considered as quite toxic. Thus, solvents utilizable for this reaction are preferably hydrocarbons which contain five to twenty-four carbon atoms and pure hydrocarbons such as pentane, hexane, heptane, octane, benzene and their isomers can be used. Petroleum fractions known as petroleum ethers boiling in the range of 40°-60° C., 60°-80° C. and more preferably those boiling in the range of 80°-120° C. were also found to be good solvents as were the petroleum fractions known as gasoline, naphtha and kerosene.

While the solvents used for this reaction can be in proportions ranging from 2 to 10 parts by volume per part of the vinyl aromatic compound especially preferred are proportions ranging from about 2 to about 5 parts per part of the vinyl aromatic compound.

The term vinyl aromatic compounds as used herein includes such compounds as styrene, α-methyl styrene, vinyl toluene, vinylxylene, ethyl vinyl benzene, t-butyl styrene, divinyl benzenes, isopropylstyrene, chlorostyrenes, dichlorostyrenes, bromo styrenes, ring substituted methoxy styrenes, etc. The preferred vinyl monomer is styrene.

One of the advantages of the unitary process of the present invention is the fact that the reaction can utilize styrene per se or more economically can be carried out with styrene containing streams. Such a styrene containing stream is the C-8 aromatic fraction having a boiling range of about 120°-150° C. produced by the stream cracking of naphthas to produce ethylene. This C-8 aromatic fraction consists essentially of about 15 to 50% by weight of styrene, from 5 to 25% by weight ethyl benzene and about 30 to 80% by weight of mixed xylene isomers.

It has been found according to the present invention that by reacting such as C-8 aromatic stream consisting of a 1:2 C-8 fraction: solvent mix in the presence of an azo radical initiator with HBr at 80°-95° C. that only the styrene reacts to form beta bromoethyl benzene. The remaining other components of the C-8 aromatic fraction were easily separated by fractional distillation from beta bromoethyl benzene. Furthermore, the resulting C-8 aromatic fraction which is styrene-free is of greater value and could be used without any further treatment in a gasoline pool or for xylene extraction. By reacting the C-8 fraction with HBr there is thus inexpensively produced beta phenethyl bromide and at the same time an upgraded C-8 aromatic fraction. The presence of styrene in gasoline causes the formation of gums in the carburator and polymerizes during the extraction techniques practiced to isolate the pure xylenes and it is for this reason that the process of the present invention has commercial advantages and significance also in this field. While the reaction can be carried out in a temperature range of about 60°-120° C. preferred is a temperature range of about 70°-100° C. and especially preferred is a temperature range of about 80°-95° C. as stated above.

As stated the reaction is carried out in the presence of azo radical initiator compounds to effect the anti-markovnikoff addition of HBr to the olefin. Azo compounds of the general formula

where $R_1$ and $R_2$ are each the same or different and represent an acyclic and or cyclic aliphatic chain containing at least two carbon atoms each and optionally containing an electron withdrawing group such as nitrile groups are especially preferred. Such compounds include, e.g., azo bis-isobutyronitrile, azo bis-dimethyl isoaleronitrile and 1,1'azo dicyclohexane carbonitrile.

A preferred azo compound is azo bis-isobutyronitrile.

The quantities of the azo radical initiator are in the range of 0.1 to 5 and preferably from 0.5 to 2 weight percent of the olefin used. The combination of azo compounds with other radical initiators or in the presence of UV light could also be used.

While the invention will now be described in connection with certain preferred embodiments in the following examples, it will be understood that it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of procedures as well as of the principles and conceptual aspects of the invention.

EXAMPLE 1

In a two liter reaction flask 200 g styrene were mixed with 800 ml of heptane and 2 g azo bis-isobutyronitrile. When HBr is bubbled the reaction temperature was raised and maintained at 80°–95° C. The HBr stream was bubbled at a rate of 750–1200 cc/minutes. After 1 hour the reaction mixture was saturated with HBr. By g.l.c. analysis 99.7% of styrene was reacted to produce 353 g beta-bromoethyl benzene isolated by vacuum distillation of 92° C./11 mm Hg. The α-bromoethyl benzene was less than 0.1% as measured by g.l.c. analysis. The yield to the beta-bromoethyl benzene was 99.5%.

COMPARATIVE EXAMPLE 1a

For purposes of comparison, the same experiment as in Example 1 but instead of azo isobutyronitrile 2 g of benzoyl peroxide were added with 600 ml of CCl$_4$. The reaction rate was slower. After 4 hours complete saturation with respect to HBr was obtained. The reaction product analyzed by g.l.c. contained 25% α-bromo and 75% beta-bromo ethyl benzene. We have performed more experiments increasing the amount of benzoyl peroxide. Only a concentration of about 9 weight percent based on the styrene prevented the formation of the α-isomer.

This example shows that when using benzoyl peroxide at the same concentration level as azo bis-isobutyro nitrile, large amounts of the alpha-bromo isomer are formed.

EXAMPLE 2

500 g of a C-8 aromatic fraction which contained 35% styrene were mixed with 600 ml of heptane and 2 g azo bis-isobutyronitrile and reacted as described in example 1. After 1 hour reaction time N$_2$ was bubbled to displace the dissolved HBr. The reaction mixture was subjected to fractional distillation collecting heptane as first fraction and 315 g of C-8 fraction of 120°–140° C. After applying vacuum 307 g of beta bromo ethyl benzene were collected at 90°/10 mm g.

EXAMPLE 3

In the same reaction flask as described in example 1, 200 g of vinyl toluenes, 800 ml of petroleum ether having a boiling range of about 100°–120° C. and 2 g of azo bisisobutyronitrile were reacted at 85°–95° C. with dry gaseous HBr. After 1 hour N$_2$ was bubbled to remove the dissolved HBr. Petroleum ether was stripped off. At 25 mm-Hg vacuum 270 g beta-bromo ethyl toluenes were collected at 118°–126° C.

EXAMPLE 4

As described in Example 1, 200 g of P-bromo styrene were reacted with 800 ml naphtha and 1.5 g azo bisisobutyronitrile. After 2 hours reaction at 85° C. and work up as described in example 3, 240 g of 2-bromo-ethyl bromobenzene at 80°–82° C. at 0.2 mm Hg were isolated.

EXAMPLE 5

In a manner similar to that described in Example 1, 200 g styrene were mixed with 800 ml kerosene and 2 g azo bis-dimethyl isovaleronitrile. When HBr is bubbled in, the reaction temperature was raised and maintained at 85°–90° C. After 1 hour the reaction mixture was saturated with HBr and beta-bromoethyl benzene isolated and collected by vacuum distillation is described.

While particular embodiments of this invention have been described, it will be evident to those skilled in the art that the present invention may be embodied in other specific forms without departing from the essential characteristics thereof. The present embodiments and examples are, therefore, to be considered in all respects as illustrative and not restrictive, the scope of the invention being indicated by the appended claims rather than by the foregoing description and all changes which come within the meaning and range of equivalency of the claims are, therefore, intended to be embraced therein.

What is claimed is:

1. A process for producing beta-bromo aromatic compounds comprising reacting hydrogen bromide with a vinyl aromatic compound in the presence of an azo radical initiator to effect the anti-markovnikoff addition of HBr to the vinyl double bond.

2. A process according to claim 1 wherein the amount of azo radical initiator used is about 0.1 to 5 wt% of said vinyl aromatic compound.

3. A process according to claim 1 wherein the vinyl aromatic compound is styrene.

4. A process according to claim 1 wherein said styrene is contained in and directly reacted from a C-8 aromatic fraction having a boiling range of about 120° to 150° C. and having been produced by the steam cracking of naphthas to produce ethylene, said C-8 aromatic fraction consisting essentially of about 15 to 50% by wt. styrene, from 5 to 25% by weight ethyl benzene and about 30 to about 80% by weight mixed xylene isomers.

5. A process according to claim 1 wherein the reaction is carried out in the presence of a non-polar solvent containing from about 5 to about 24 carbon atoms.

6. A process according to claim 1 wherein the reaction is carried out in the presence of a solvent selected from the group consisting of gasoline, naphtha, kerosene and petroleum ether.

7. A process according to claim 1 wherein the reaction is carried out in a straight or branched chain hydrocarbon solvent having from about 5 to about 24 carbon atoms.

8. A process according to claim 5 wherein the ratio of solvent to vinyl aromatic compound is about 2:1 to about 10:1 parts by volume.

9. A process according to claim 1 wherein the azo radical initiator is azo bis-isobutyronitrile.

* * * * *